United States Patent [19]

Caporiccio et al.

[11] 4,254,030

[45] Mar. 3, 1981

[54] FLUOROSULPHONYL OXAFLUOROALKANES FLUOROSULPHONYL OLEFINES AND PROCESSES FOR THEIR PREPARATION

[75] Inventors: Gerardo Caporiccio; Gianangelo Bargigia; Giampiero Guidetti, all of Milan, Italy

[73] Assignee: Montedison S.p.A., Switzerland

[21] Appl. No.: 19,006

[22] Filed: Mar. 9, 1979

Related U.S. Application Data

[62] Division of Ser. No. 821,394, Aug. 3, 1977, Pat. No. 4,180,639.

[30] Foreign Application Priority Data

Aug. 6, 1976 [IT] Italy .............................. 26116 A/76
Mar. 2, 1977 [IT] Italy .............................. 20831 A/77

[51] Int. Cl.$^3$ .................... C07C 143/70; C08F 28/02
[52] U.S. Cl. ............................. 260/543 F; 204/242; 526/243
[58] Field of Search ................................ 260/543 F

[56] References Cited

U.S. PATENT DOCUMENTS

| | | | |
|---|---|---|---|
| 3,555,080 | 1/1971 | Resnick | 260/513 F |
| 3,821,290 | 6/1974 | Anello | 260/513 R |

*Primary Examiner*—C. A. Henderson
*Attorney, Agent, or Firm*—Hubbell, Cohen, Stiefel & Gross

[57] ABSTRACT

A new class of fluorosulphonyl oxafluoroalkanes and their derivatives is disclosed as well as a process for preparing said products. Furthermore, a new class of fluorosulphonyl olefins, copolymers thereof and a process for preparing same is also disclosed.

11 Claims, No Drawings

FLUOROSULPHONYL OXAFLUOROALKANES FLUOROSULPHONYL OLEFINES AND PROCESSES FOR THEIR PREPARATION

This is a division, of application Ser. No. 821,394, filed Aug. 3, 1977, now U.S. Pat. No. 4,180,639.

THE PRIOR ART

The perfluoroalkansulphonyl halides are well known in the art. One of the most typical uses of this kind of precursor is in the field of agents endowed with superficial activity. They may be prepared, for instance, by electrochemical fluorination in an anhydrous liquid hydrofluoric acid of a suitable sulphonyl $-RSO_2Z$ wherein R is an alkyl group and Z is a halogen.

By this process all the hydrogen atoms are substituted by fluorine atoms, and in the case where there were other halogen atoms present, they are similarly substituted by fluorine atoms.

According to another method of preparation, compounds of the formula $C_nF_{2n+1}-SO_2Cl$ may be prepared by oxidizing perfluoroalkansulphinic acids with chlorine, the former being obtained by inserting an $SO_2$ into a $C_nF_{2n+1}MgBr$ molecule which in turn is obtained from the corresponding perfluoroalkaniodides.

According to a third process, the sulphonyl fluorides are obtained by addition of $SO_2F_2$ to the double bonds of a perfluoroalkene.

According to the first two methods described above, when starting with molecules that are of a pre-fixed length, the intended compound is prepared by substituting hydrogen atoms with fluorine atoms when the molecule already contains the $SO_2Z$ functional group $-SO_2Z$, or by inserting the $SO_2Z$ functional group when the molecule is already perfluorinated.

In the first case, in spite of the improvements introduced, the yields are rather poor and the reactants are products that are not very common.

In the second case the method is rather complex and delicate.

As far as the third method is concerned, perfluoroalkenes with more than three (3) carbon atoms in the choir chain are unusual and, if one desires molecules of the formula $C_nF_{2n+1}SO_2Z$ with n greater than 2, there are obtained exclusively derivatives with the $SO_2F$ functional group substituted laterally in position 2 with respect to the linear chain, that is, no linear compounds are obtained.

Another class of compounds that are particularly important in the technique are the perfluorinated olefins that also contain the functional sulphonyl group: $-SO_2Z$.

It is known that the formation of the double bond which is present in the perfluorinated olefins containing in the chain ether bridges and functional reactive groups, may be obtained by pyrolysis of alkal salts of perfluoro-alkancarboxylic acids, which lose one mole of carbon dioxide and one mole of alkali fluoride thus producing the unsaturation. In U.S. Pat. No. 3,180,895 there is described the decarboxylation of compounds of the formula:

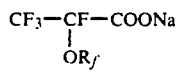

wherein R is perfluorinated alkyl radical.

However, the operational conditions required for all these reactions are rather strict and if there are only traces of water present the undesired formation of saturated hydrogen containing by-products of the type $R_fO-CFH-CF_3$ occurs.

Of particular complexity is the obtainment of perfluorinated olefins when it is desired to have the presence of a second reactive function besides the double bond (see R. Sullivan, J. Org. Chem. 34, 1841, 1969). Among the fluorinated olefin containing functions other than the double bond, of particular interest are those containing a sulphonic or a fluorosulphonylic functional group, inasmuch as they are endowed with exceptional chemical and thermal stability. These latter olefin are usually obtained according to two methods:

(1) by adding $SO_2F_2$ to diolefins, as for instance $CF_2=CFO(CF_2--CF_2O)_m-CF=CF_2$, and operating in such a way as to introduce only a single mol of $SO_2F_2$ per mol of diolefin; or (2) by adding hexafluoropropylene-oxide to fluorosulphonyldifluoroacetyl fluoride and by decarboxylating the product

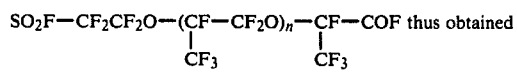 thus obtained (Du Pont Innovation vol. 4 no. 3 (1973) pages 10–13).

Method (1) requires the use of little used and expensive reactants and has the drawback of allowing the introduction of the $-SO_2F$ unit exclusively in position 2, wherefore it becomes impossible to obtain products having a linear chain.

Method (2), besides carrying branched products, has the drawbacks resulting from the very drastic operational conditions required in such a process with regard to the formation of saturated products. Moreover this method requires the use of hexafluoropropylenoxide, which is obtainable only in poor yields and with a certain difficulty (see J. Macr.Sci.Chem. A6(6), page 1027–1052, (1972) and U.S. Pat. Nos. 3,775,438). Moreover the addition of hexafluoropropylenoxide to the $-COF$ group must be carried out at particularly low temperatures in order to avoid concomitant chain transfering reactions, wherefore there are required solvents such as tetraglyme $CH_3O(CH_2CH_2O)_4CH_3$ and nucleophilic agents such as CsF both of which are, particularly uncommon and expensive substances. In any case it is not possible, even if desired, to obtain, by this process, sequences of perfluorinated carbon atoms greater than 2, inasmuch as, by such a reaction, it is impossible to insert perfluorinated olefin molecules but only epoxides.

THE PRESENT INVENTION

Object of this invention is that of eliminating the above listed drawbacks and to find a new class of oxafluoroalkansulphonic iodine-substituted fluorides and the corresponding perfluorinated sulphonates.

Another object of this invention is that of eliminating the above cited drawbacks and to find a class of fluorinated olefines containing in a chain both ether bridges as well as reactive functional groups and that be capable of copolymerizing with commercial olefines and/or fluoroolefines. The fluorinated olefines that have reactive functional groups allow to modify the cross-linking systems of the fluoroelastomers.

Still another object of the invention is that of preparing compounds of the general formula:

$$ZSO_2-\underset{X}{CF}-CF_2-O-CF_2-\underset{X}{CF}(CF_2CF)_m-(CF_2-CF_2)_{n-1}-Y \quad (A)$$

wherein

Y=H, Cl, Br, F, I, $CF_2$-COOH, $CF_2CONH_2$, $CF_2COCF_3$, $CF_2(CH_2)OH$, $CF_2CH_2NH_2$, $CF_2CH_2CF_3$, $CF_2COOR'$ and
$CF=CF_2$ wherein $R'$ is an alkyl containing up to 6 carbon atoms or a phenyl.

It has now surprisingly been found that the product of general formula (A), wherein Y=I, Z=F, m=0 (zero) and n=1, behaves like a normal iodoperfluorinated telogen (e.g.: $C_2F_5I$), that is, like a molecule generating radicals capable of summing themselves to fluorinated olefines such as for instance $C_2F_4$, $C_6F_6$ and $C_2ClF_3$, generating the corresponding telomers, as schematized in equation III given hereunder, without giving secondary reactions of addition of the $-SO_2F$ group on the double bond of the perfluoroolefine, as on the contrary is characteristical for the $SO_2F_2$ compound.

To the general formula (A) belong new linear or branched olefines with an oxaperfluorinated chain, which are provided with a sulphonic or sulphonylic functional group and which proved of particular interest in as much as they have been obtained by using reactants and solvents immediately available on the market and of a low or relatively low cost.

Said fluorinated olefines show the following general formula:

$$ZSO_2-\underset{X}{CF}-CF_2-O-CF_2CF_2-(CF_2-\underset{X}{CF})_m-(CF_2-CF_2)_{n-1}CF=CF_2 \quad (B)$$

wherein
m=zero or a whole number comprised between 1 and 10, preferably between 0 and 2;
n=a whole number between 1 and 10, preferably between 1 and 4;
X is selected from F, $CF_3$, Cl and
Z is selected from F, OH, OM wherein M is a cation and OR wherein R is an alkyl containing from 1 to 8 carbon atoms on an aryl.

Part of this invention are also the copolymers of the above mentioned olefines with one fluoroolefine or mixture of fluoroolefines or mixture of a fluoroolefine and an olefine or with a chlorofluoroolefine, alone or in admixture with a fluoroolefine.

The products according to this invention are prepared by operating according to the following equations:

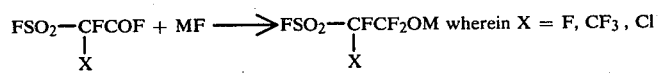  (I)

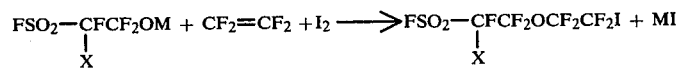  (II)

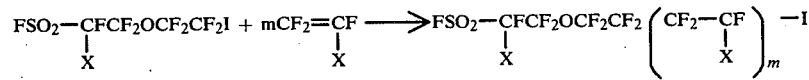  (III)

  (IV)

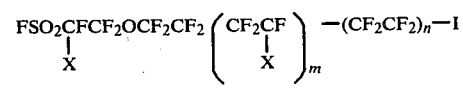  (V)

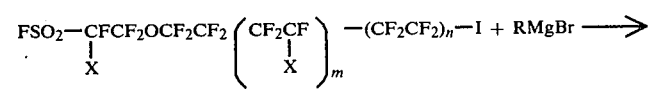

  (VI)

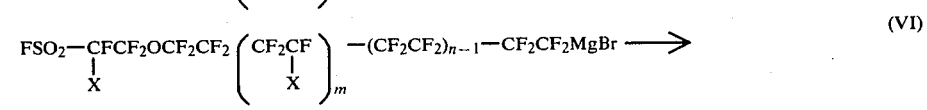

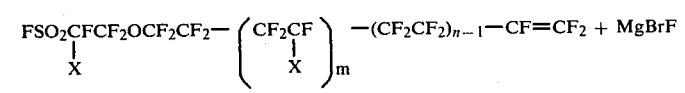  (VII)

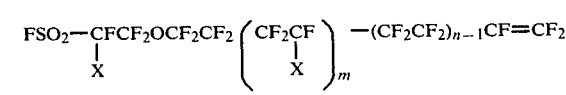

+ olefines ⟶ copolymers

The FSO$_2$—CF(X)—COF compound, indicated as starting substance in the first equation, is the fluoride of fluorosulphonyldifluoroacetic acid or the fluoride of 2-fluorosulphonyl-perfluoropropionic acid which is easily prepared by isomerization of the corresponding sultone, as indicated by Knunyants & Sokolski in: Angewandte Chemie, International Edition, Volume 11, (1972), page 583–595.

The sultone derives from the reaction of sulphur trioxide and CF$_2$=CFX, wherein X=F, Cl or CF$_3$.

According to equation (I) the fluoride of fluorosulphonyl fluoroalkyl acid was made to react with MF fluoride where M is a catione selected from alkali cationes, the silver catione and the quaternary ammonium catione. Preferably there are used the alkali fluorides and especially K and Cs fluorides. The quantity of MF must be about equimolar, e.g. comprised between 0.7 and 1.3 mols per mol of fluorosulphonyl compound, in view of the fact that an amount too low of MF would bring with it a waste of fluorosulphonyl derivative, while an amount too high would bring to the formation of excessive amount of by-products.

Reaction (I) was conducted in a liquid medium that acted either totally or partially as a solvent for the components involved in the reactions; suitable liquids are inert, polar organic solvents. Among these can be mentioned the dialkyl ethers of alkylene or the polyalkylenglycoles, the dialkylamides of lower fatty acids, the liquid nitriles and the alifatic or cycloaliphatic sulphones. Examples of such solvents are: dimethyl ethers of ethylene, diethylene and triethyleglycole ethers, dimethylformamide, dimethylacetamide, acetonitrile, propionitrile and tetramethylensulphone. The preferred solvent is acetonitrile.

The reaction (I) is preferably carried out at a temperature comprised between 20° and 30° C.

According to equation (II), the ionic compound produced in reaction (I) is treated with iodine and tetrafluoroethylene, with the formation of 1-fluorosulphonyl-3-oxa-5-iodoperfluoropentane. However, also other fluoroolefines such as e.g. CF=CFCl, behave like tetrafluoroethylene.

Reaction (II) is conducted in an autoclave. The quantity of necessary iodine amounts to two gram atoms per each mol of ionic compound; however, the yields in the reaction product (II) improve when there is used an excess of iodine, e.g. 3.0 g atoms of iodine per each mol of ionic compound. As far as the fluorinated olefines are concerned, these are introduced into the autoclave as the last, with the help of a compressor and at room temperature.

The quantity of olefines loaded into the autoclave is essentially that which is consumed in the reaction plus the quantity required for maintaining the reactor at the selected pressure. The pressure in the autoclave may vary from a pressure only just above atmospheric pressure up to 40 atm. Preferably it is operated at a pressure between 1 and 20 atm. The temperature is comprised between 0° C. and 100° C., but preferably is comprised between 10° C. and 70° C.

The formation of the radicals of the iodine-ended telogen may be started either by heating or by using radiations such as U.V. rays, or by organic peroxides e.g. ditert.butylperoxide, by benzoyl peroxide, by peracids such as peracetic acid and trifluoroperacetic acid, by azobis(iso-butyrronitrile) or by the use of complex catalysts consisting of a metal salt and an amine, e.g. CuCl-ethanolamine. To the radical coming from the splitting of the telogen there are additioned one or more molecules of fluorinated olefines.

The reaction may be directed towards telomers with a more or less high molecular weight, depending on the quantity of olefine used. In the case in which a smaller quantity of olefine is used, it will be obtained a greater quantity of unreacted telogen and a prevalence of telomers of a lower molecular weight; in the case in which there were used a greater quantity of olefin there will be obtained a smaller quantity of unreacted telogen and a prevalence of telomers of higher molecular weight.

In order to obtain particularly useful products according to this invention, it is necessary to apply a molar ratio olefine/telogen comprised between 0.5 and 4, preferably between 0.8 and 2.0.

The 1-fluorosulphonyl-3-oxa-ω-iodo-alkanes show all the reaction typical for molecules containing the functional groups —SO$_2$F and —I. The mobile iodine atom of the compounds of formula (A), wherein Y=I, may give origin to various different derivatives as for instance to those of the formula (A) in which Y has the meanings indicated before. Particularly important are considered:

(1) the substitution of the iodine atom with a fluorine atom, and respectively.

(2) the iodine atom substitution reaction by means of the exchange with alkyl-magnesium halide, which leads to the formation of the corresponding fluorinated Grignard compound (see Jour. Am. Che. Soc. 75, (1953), 2516).

The fluorinated organic compounds as obtained at the end of the equation III, thanks to the mobile iodine atom, are highly reactive and may be converted to numerous and useful compounds; thus, for instance, there may be prepared fluorides of oxa-fluoroalkan-sulphonic acids through the reaction with fluorine according to the following equation:

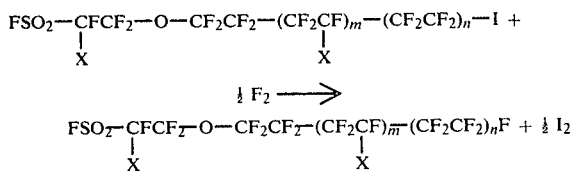

The displacement of one iodine atom by a fluorine atom occurs preferably at about 0° C., but in general at between −10° C. and about +50° C. Preferably it is operated at atmospheric pressure or at a pressure slightly greater than atmospheric pressure, and in the presence of a liquid solvent and a gaseous diluent for fluorine, for instance nitrogen, argon or their mixtures. A suitable solvent consists of trichloro-trifluoroethane.

Another fluorinating solvent consists of chlorine trifluoride. The fluorides may be conveniently converted to the corresponding sulphonates by alkaline hydrolysis, and successively may be converted to the corresponding free sulphonic acids; or they may be usefully converted to amino-alkyl-amides having, for instance the following formula:

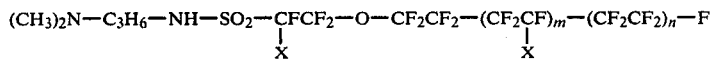

and being completely similar to the amino-alkyl-amides described by Guenthner and Victor (Industrial & Engineering Chemistry, Product Research & Development; vol. 1, no 3, Sept. 1962, page 165). These amidic compounds may be successively converted, as it is well known, to other derivatives such as for instance to internal salts of the formula:

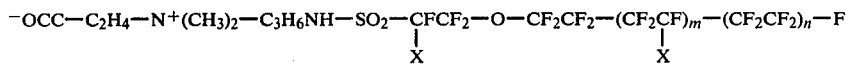

The alkaline sulphonates and the sulphonic acids mentioned above, containing an atom of ether oxygen, develop a surfactant activity that is definitely more pronounced than that of the corresponding compounds lacking ether groups.

The same alkaline salts of the fluorosulphonic acids are used for highly corrosive electrolytic baths and for pickling baths for stainless steels. The free acids are very active catalysts for some reactions, e.g. for esterification reactions; the above mentioned amino-alkyl-amidic derivatives may be used as surfactants also in non-aqueous media. The process according to the invention allows to conveniently obtains said fluorides of oxa-fluoroalkan-sulphonic acids and their corresponding sulphonates, by making recourse to a very common and easily available raw material such as for instance tetrafluoroethylene. Moreover, the reactions envisaged by this invention do not show the drawbacks of electrochemical fluorination. The yields are high and there appear by-products only in slight quantities.

Other examples of the transformation of the products of formula (A) wherein $Y=I$, $m=$zero, $X=F$ and $Z=F$, are represented by the following equations:

$FSO_2-CF_2CF_2-O-CF_2CF_2-(CF_2CF_2)_n-I + CISO_3H \rightarrow$ $\rightarrow FSO_2+CF_2CF_2-O-CF_2CF_2-(CF_2CF_2)_n-OSO_2Cl + HI$ $FSO_2-CF_2CF_2-O-CF_2CF_2-(CF_2CF_2)_n-OSO_2Cl + 3H_2O \rightarrow$ $\rightarrow FSO_2-CF_2CF_2-O-CF_2CF_2-(CF_2CF_2)_{n-1}-CF_2COOH + 2HF + HCl + H_2SO_4$ $FSO_2-CF_2CF_2-O-CF_2CF_2(CF_2CF_2)_n-OSO_2Cl + 6NH_4OH \rightarrow$ $\rightarrow FSO_2CF_2CF_2-O-CF_2CF_2-(CF_2CF_2)_{n-1}-CF_2CONH_2 +$ $+ (NH_4)_2SO_4 + NH_4Cl + 2NH_4F + 4H_2O.$ Besides the uses already cited for the compounds according to this invention and for their derivatives, there must be mentioned also the possibility of making water- and oil-repellent a great number of different materials and in particular fibres and fabrics. Moreover, it is possible to realize stable foams, durable also in the presence of aggressive chemical substances which would destroy the greatest part of common surfactants. Last but not least, they may be used as additives with a surfacting action for paints, waxes, cosmetics, and adhesives or as release agents.

The fluorinated Grignard compounds are stable only at very low temperatures (of the order of $-70°$ C.) and they decompose so much the faster the more one moves away from the low temperatures. The composition products of the fluorinated Grignard compounds are olefines of a different type, both due to the position of the double bond as well as for the presence of different substituents in place of fluorine atoms.

A particularly important aspect of this invention is that of having realized a process which allows to obtain the new olefines with excellent yields and free of by-products, avoiding any interaction between the terminal group $-SO_2F$ and Grignard compounds, on the other hand also avoiding secondary reactions between the different species present during the course of the reaction.

The process for the preparation of the fluorinated olefines of this invention is characterized in that an alkyl halide or phenylmagnesium halide are slowly and gradually added by portions to the solution of fluorosulphonyl-oxa-perfluoroalkaniodide in tetrahydrofurane, maintained at a temperature comprised between $-20°$ C. and $+20°$ C., but preferably at $0°$ C.; in that the mixture is heated up to $25°-30°$ C. at such a reduced pressure as to get a vigorous boiling and the entraining of the product of reaction together with the solvent into a suitable collecting tank wherein the solvent is reintegrated and whereafter the operation is repeated adding successive portions of alkyl or phenyl-magnesium halide up to the total consumption of the reacting iodide.

The fluorinated olefines of this invention are colourless liquids, and they have an average molecular weight comprised between 400 and 800, and a density of about 1.8 g/cc at $20°$ C.

They are used as comonomers in the copolymerization with fluoroolefines, chlorofluoroolefines and mixtures of fluoroolefines and olefines.

The copolymerization is carried out by reacting the fluorinated olefine of the above indicated general formula (B), after previously dissolving in a perfluorocarbon or chlorofluoro carbon solvent, with at least one of the above indicated defines, in molar ratios comprised between 1:99 and 25:75, in the presence of a free radicals initiator. In general one operates at a temperature comprised between 40° and 170° C., although also temperatures outside this range may be applied. As a radical initiator may be used any organic peroxide. Preferably there is used benzoyl peroxide, tert.butyl peroxide and bis(4-tert.butylcyclohexyl) peroxydicarbonate.

The peroxide is used in a quantity comprised between 0.05 and 1.5% by weight, referred to the reactants.

The fluoroolefines and chlorofluoroolefines preferably used in the copolymerization of this invention are e.g.: tetrafluoroethylene, hexafluoropropene, vinyl fluoride, vinylidene fluoride and chlorofluoroethylene, either alone or in admixture with each other or with perfluoroalkyl vinylethers. The olefines preferably used in the copolymerization are ethylene and propylene.

The copolymers of this invention have a molecular weight comprised between 10,000 and 3,000,000, but preferably are comprised between 20,000 and 1,000,000. They contain an oxaperfluorosulphonic olefine in a quantity of from 0.1 to 10% by mols, preferably from 0.5 to 5% in mols, referred to the mols of all the enchained olefine units.

The copolymers of this invention form a material particularly suitable for the preparation of permoselective membranes that are particularly resistant against oxidizing agents and may be used for chemical and electrochemical processes. There have been prepared membranes from a film based on polytetrafluoroethylene and on the copolymer of this invention and having a thickness of 6-8 mils, which membranes have given excellent results in electrolytic cells for the production of chlorine and soda from aqueous sodium chloride solutions.

More particularly, the fluorinated olefines of general formula (A), wherein Z=OH, that is, the sulphonic acids, are used also in the preparation of new elastomeric copolymers which are cross-linked by means of oxides or alkaline basic salts, with the formation of saline bonds on the side links of the chain.

This type of cross-linking represents a doubtless technical progress in as much as it does not involve the main chain of macromolecules. The cross-linked elastomers thus obtained display excellent resistance against heat, a good stability to heat and a good resistance to chemical agents. They are suitable for seals, gaskets, grommets and other similar articles.

The following examples are given for purely illustrative and non limiting purposes of the scope of this invention.

EXAMPLE 1

Into a three-necked, 1 liter pyrex glass flask, fitted with a reflux condenser a stirrer and a dropping funnel, and containing 750 cc of anhydrous acetonitrile and 45.2 g of anhydrous potassium fluoride (0.78 mol) in the form of a fine powder, and maintained in a bath stabilized at 20° C., there were introduced during a 1 hour period and under stirring 140.5 g (0.78 mol) of fluorosulphonyl-difluoro acetyl fluoride. After completing the addition, the mixture was kept under stirring for another 60 minutes.

Thereby was obtained the ionic compound $FSO_2—CF_2CF_2—OK$. This compound was thereupon introduced into a 2 liter autoclave made of Hastelloy, into which had been introduced 297 g of dry elemental iodine (2.34 g atoms).

The temperature was set at 20° C. and, after having stirred the mixture for 60 minutes, by means of a compressor tetrafluoroethylene was introduced into the autoclave at 20 atm. The reaction mass was then left under stirring for 4 hours during which the pressure dropped to 2-3 atm. The residual gases were exhausted and the liquid content was carefully poured over 3,000 g of a mixture of water and ice.

A dark solution was obtained, (dark due to the presence of unreacted iodine) and it was decolorized with 600 cc of a 1 molar sodium sulphite solution.

The organic layer was heavier than the aqueous layer and was thus separated from the bottom; after drying with sodium sulphate, there were obtained 260 g of raw material.

By fractional distillation of the raw material in an automatic apparatus, there separated a first fraction of 28 g having a boiling point between 24° and 27° C. at 100 mmHg, prevailingly consisting of the reaction solvent. The pressure was then reduced to 70 mmHg and a second fraction of 50 g was gathered which had a boiling point of up to 45° C. and being prevailingly formed of tetrafluorodiiodoethane.

The remaining residue was quickly distilled at 2 mm Hg. By condensation in a trap cooled with a mixture of acetone-dry ice, there were obtained 179 g of $FSO_2CF_2CF_2OCF_2CF_2I$. This is a colorless liquid which becomes violet under the action of light and had a boiling point of 123° C. at 750 mmHg.

The mass spectrometer showed a molecular ion of mass 426.

The nuclear magnetic resonance analysis for $^{19}F$ gave the following signals (chemical shifts$\delta$, ppm from $CFCl_3$): 46.5($F-SO_2—$); $-65.5(—CF_2-I)$; $-83.5(FSO_2CF_2CF_2-O—)$; $-86.5(—OCF_2-CF_2I)$; $-114(FSO_2CF_2--)$.

The results of the integration of the NMR spectra are in accordance with the number of fluorine atoms foreseen for each peak.

EXAMPLE 2

Into a 200 ml stainless steel autoclave were introduced 70 g (0.164 mol) of $FSO_2—CF_2CF_2OCF_2CF_2I$ obtained as described in example 1.

After cooling the autoclave in liquid nitrogen, there were added 30 g (0.30 mol) of tetrafluoroethylene. The system was then brought up to room temperature and the autoclave was then heated for 6 hours at 180° C. in an oil bath and under rocking. After having been cooled, the autoclave was degassed and then opened. From it there were extracted 95 g of a semifluid white product which was quickly distilled at 0.5 mmHg so as to get a liquid fraction as the head and a solid fraction as a residue. The liquid part was then further subjected to fractionation at a pressure of 40 mmHg in an automatic apparatus.

As a head there separated 27 g of unreacted $FSO_2C_2F_4—O—C_2F_4I$; as tails there remained 50 g of telomers of the formula:

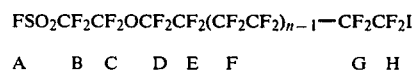

wherein: n=a whole number between 1 and 4.

Analyzing by means of the NMR for $^{19}F$ the signals corresponding to the F atoms of the groups indicated by A, B, C, in the molecule of the telomer they correspond to the signals of the same groups in the molecule of the telogen $FSO_2—C_2F_4—O—C_2F_4I$ as described in example 1.

For the other groups D, E, F, G, H the chemical shifts (ppm from $CFCl_3$) turned out to be respectively equal to: $-84.5$; $-126$; $-123$; $-115$; $-59$.

By sublimation of the solid fraction, there was obtained a product with an average molecular weight of 890 and a residue of average molecular weight 1050. The formulae have also been confirmed by IR spectra.

EXAMPLE 3

Into a pyrex glass reactor fitted with a gas inlet, a gauge and a safety valve, containing in the center a high pressure mercury Hanau lamp for the generation of U.V. radiation, protected by a sheet of quartz, there were introduced 10 g (0.0235 mol) of $FSO_2$—$CF_2$—$CF_2$—O—$CF_2CF_2I$ telogen obtained as described in example 1. The temperature was set at 15° C. and gaseous hexafluoropropylene was introduced into the reactor under a pressure of about 1.1 ata.

Once saturation was achieved, the mercury lamp was lighted.

After 20 hours the liquid was extracted and subjected to fractional distillation:

The head fraction (at 48° C./40 mmHg) weighed 7.5 g and consisted essentially of unreacted telogen. The residue contained 10% of unreacted telogen and a mixture of telomers of the formula:

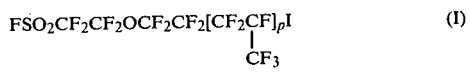   (I)

wherein the average value of p is 1.1 and prevailingly is equal to 1. This preceding formula was also confirmed by NMR analysis.

EXAMPLE 4

Into a 10 ml pyrex glass vial were introduced 3.2 g of telomers (1) obtained as described in example 3.

The vial was then cooled in liquid nitrogen and was put under vacuum. By gaseous transfer under vacuum, there were additioned 0.55 g of tetrafluoroethylene.

The vial was sealed and heated in an oil bath, stabilized at 180° C., for 6 hours, while it was kept under stirring with a rocking movement.

After cooling down to room temperature, the vial was dipped into a bath of dry ice and acetone and there carefully opened and its content (3.8 g) fractioned into two parts by distillation in a bath of 100°–140° C. and under a pressure of 1 Torr. Thereby were gathered 1.6 g of a first fraction (bath at 100°–110° C.) consisting of 12% of $FSO_2$—$C_2F_4$—O—$C_2F_4I$. In the second fraction, distilled in the bath up to 140° C. and consisting of 1.8 g of substance, there were identified by nuclear magnetic resonance of $^{19}F$ and by mass spectrography in association with gas-chromatography, the telomers $FSO_2$—$C_2F_4OC_2F_4(C_2F_4)_nI$ with n comprised between 1 and 4 and the telomers $FSO_2$—$C_2F_4OC_2F$—$C_3F_6$—$(C_2F_4)_m$—I wherein m was comprised between 1 and 3.

The various telomers, for the values of n between 1 and 4 and for the values of m between 1 and 3, showed respectively, at the mass spectrometry analysis, molecular ions of mass: 526; 626; 726; 826; 676; 776; 876; moreover they showed a fragmentation that was in accordance with the structure.

EXAMPLE 5

Into a 1000 cc, heat stabilized flask, fitted with a reflux-condenser, were introduced 700 cc of anhydrous 1,1,2-trichlorotrifluoroethane, 70 g of NaF, 70 g of $MgF_2$ and 32 g of the mixture of telomers obtained according to example 2.

The flask was deaerated and then cooled down to 0° C. while the vapours were condensed by refluxing at −20° C.; thereupon there were introduced, under a liquid head, 10 lt/hr of a mixture of nitrogen and fluorine, free of hydrofluoric acid, according to a molar ratio $N_2:F_2 = 3:1$.

As a safety measure, the gases flowing out of the reactor were made to pass through a sulphur oven for the total destruction of the unreacted fluorine in excess. After 3 hours the flow of the fluorine was suspended while the nitrogen was allowed to flow on in order to eliminate the last traces of halogen. There was then added a 10% aqueous solution of sodium carbonate until attaining a neutral pH. Thereupon the insoluble salts are filtered and then the organic layer is separated by gravity since it is heavier than the aqueous phase. The solvent was distilled in a Vigreux column and from the bottom of this latter was gathered a mixture of fluorides of oxa-perfluoro-alkan-sulphonic acids of formula:

wherein the symbols have the sme meaning as in example 2.

The formula was confirmed by the instrumental analyses (I.R. and NMR). The mixture of fluorides indicated above was then treated for 10 hours at between 60° and 70° C., in a pyrex glass 110 cc flask, with 50 cc of a 20% aqueous solution of potassium hydrate. By aqueous decanting a solid separated which was washed with diluted hydrochloric acid and then subjected to an extraction process with methanol. On removing the solvent there remained 19.5 g of a white crystalline salt, free of iodine, of formula: $KSO_3$—$CF_2CF_2$—O—$CF_2CF_2$—$(CF_2CF_2)_n$—F.

This mixture of potassium salts of oxa-perfluoroalkan-sulphonic acids with a different chain length, show pronounced surfactant properties. An aqueous solution containing 0.05% of potassium salts has a surface tension reduced to 23 dine/cm. The perfluorooctansulphonic acid or its potassium salt, at the same concentration, have a surface tension greater than 40 dine/cm (see Guenther & Victor; "Industrial Engineering Chemistry Product Research and Development"—vol. 1, No. 3, September 1962; page 166).

The NMR analysis of fluorine 19, carried out in trifluoroacetic acid (saturated solution) showed the following chemical shifts δ(ppm from $CFCl_3$):

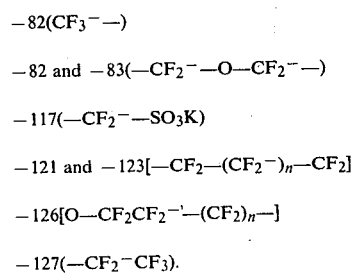

The results of the integration of the spectra are in accordance with the number of fluorine atoms foreseen for each signal. Subsequently, from the potassium salts were obtained the corresponding oxa-perfluoro-sulphonic acids.

EXAMPLE 6

12 g of the mixture of telomers obtained according to example 2 were mixed to 15 cc of chlorosulphonic acid ($ClSO_3H$).

This mixture was then cooled down to −80° C. while the pressure was reduced down to 1 mmHg of absolute pressure. At this point the vessel was hermetically sealed and then heated for 18 hours at between 140° and 145° C., under constant rocking. The mixture was then again cooled down to −80° C., the gases were discharged and the mixture was filtered on sintered glass. The organic phase, as being heavier than the excess of chlorosulphonic acid, was recovered by a separator funnel, then rectified and added to 5 cc of anhydrous methanol.

The whole was then allowed to boil for 1 hour and was then neutralized with sodium metoxide. A mixture of telomers was thus obtained which may be represented by the formula:

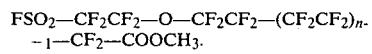

The NMR analysis of these telomers leads to results that are substantially equal to those of example 2; there was noted some slight difference for the chemical shifts characteristical for the last $CF_2$ groups on the right hand of the formula.

EXAMPLE 7

A 30% solution of chromic anhydride was prepared containing 0.3% of sulphuric acid containing 0.1% of the mixture of potassium salts of oxa-perfluoroalkansulphonic acids obtained according to example 4.

With this solution there was prepared an electrolytic chromium-plating bath of 1000 liters. In this bath were then chromium-plated objects of different shapes as well as flat plates. A suction hood is overhanging the bath. The bath is kept working for a month, checking regularly that the concentration of the electrolites and of the surfactant be constant, by means of analyses and by suitably refilling the ingredients.

There is also continuously carried out a quality and thickness control of the chromium layer deposited on the objects, while there are carried out analyses of the air sucked up by the hood overhanging the bath in order to check and determine the presence of chromates as aerosol.

With the addition of the surfactant there forms a light layer of white foam over the surface of the bath. The quality of the deposit chromium on the objects and on the flat sheets immersed in the bath is excellent, compact, shiny, not porous while the concentration of $Cr^{+++}$ in the electrolite never exceeds 0.02%. This is a sign of good stability of the bath in the presence of the surfactant. The sucked up air does not contain more than 0.001 mg of $CrO_3$/cc of air.

This is due to the barrier effect exerted by the surfactant with regard to the electrolite which is entrained out of the bath as an aerosol by the oxygen that develops in the bath.

EXAMPLE 8

It is known that the pickling of the stainless steels is so much more difficult the greater the number of alloy components and their quality, in as much as the surface layer of oxides to be removed is rather heavy, of considerable thickness and impenetrable to the acids. The exothermy of the pickling reaction brings, moreover, the temperature of the system to much higher values than are those of the room temperature.

In this case proved particularly useful the mixtures of nitric acid and hydrofluoric acid, in the presence of an efficient surfactant resisting to the attacking medium.

In this example has been described a pickling test in the presence of the surfactant described in example 5 and being of the formula: $KSO_3—C_2F_4—O—C_2F_4(C_2F_4)_nF$ wherein n is comprised between 1 and 4 and has an average value equal to about 1.25.

On an aqueous solution consisting of 25 parts of nitric acid, 19 parts of hydrofluoric acid and 56 parts of water and containing 0.05% by weight of the surfactant obtained as described in example 5, there was determined the superficial tension by means of a De Nouy tensiometer with platinum ring and there was obtained a value of 19.6 dyne/cm. After 8 months, a new determination on the same solution showed that the value of the surface tension has remained unaltered; this proves that the surfactant possesses an excellent chemical resistance.

Some metal plates (40×25×3 mm), obtained by cold milling AISI/316 stainless steel, after annealing at 1000° C. followed by a rapid quenching in water, appeared covered up by a compact bluish-grey coating with brown spots.

One such plate was introduced into a bath lined with polytetrafluoroethylene containing the herein above described solution heated at 50° C. After 4 minutes the plate was taken out of the bath and was washed with water; it appeared uniformly silverish and glazy. Repeating the test with dipping times of: 60 and 30 seconds, it was noted that in the first instance there remained very small bluish spots in the irregularities of the piece, while in the second instance said spots are of a greater size. However, the flat surfaces are perfectly silverish.

As a countertest, other metal plates were submitted to picking that had suffered the same mechanical and thermal treatment, and they were put into a bath similar to the preceding one but without the surfactant.

After 4 minutes the plate was extracted and showed to have lost the dark coating and appeared to be very similar to the plate treated in the bath that contained the surfactant.

On the contrary the plates that were immersed for respectively 60 and 30 seconds showed a decidely worse aspect. In fact there could be observed more extensive spots that were present also on the flat surfaces.

In particular the plate that remained in the bath for 30 seconds does not appear perfectly silverish in as much as there persists a slight dull patina of oxides uniformly distributed.

EXAMPLE 9

Into a 250 cc pyrex glass flask, which had been deaerated and was fitted with a condenser, a dropping funnel, and connected to the vacuum line (through a trap cooled down to −80° C.) and to the inert gas line, and fitted with a magnetic stirrer, there were introduced 11 g of a mixture of telomers prepared according to example 2 and consisting of the members wherein n=1, 2, and 3 and which are dissolved in 200 ml of dry tetrahydrofurane. The mixture was then cooled to 0° C. and to it were slowly added 5 ml of a 1 normal solution of $C_2H_5MgBr$ in tetrahydrofurane. The whole is then allowed to warm up spontaneously to 20° C., then the pressure was reduced to 100 mmHg so that there be a lively boiling, and the absorbed heat was reintegrated by immersion in a water bath. Thereby were removed about 60 ml of solvent which were gathered in the trap cooled to −80° C.

The solvent was then reintegrated and, after again cooling down to 0° C., there were added further 5 ml of the same solution of C₂H₅MgBr and the treatment was repeated as previously described. The operation is repeated until reaching globally 20 ml of C₂H₅MgBr; after the last addition of the ethyl magnesium bromide, by distillation at reduced pressure were removed and gathered in the trap cooled at −80° C., 200 ml of solvent instead of 60 ml, which were removed after the first additions of C₂H₅MgBr. The content of the trap was then treated with double its volume of H₂O:HCl in a 10:1 ratio.

The heavy layer was washed with water and then was distilled. Thereby were obtained 7.6 g of a colourless liquid having an average molecular weight of 420 and a density at 20° C. of 1,8 g/cc.

The I.R. absorption showed at 5.6 micron the characteristical band of the fluorinated olefines. At the mass spectrometer there were evidenced the mass molecular ions 380; 480; 580; 680.

The gas-chromatographic analysis did not reveal any significant quantities of by-products.

The NMR analysis is in accordance with formula:

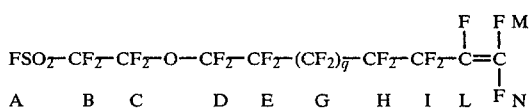

```
                               F  F M
                               |  | |
FSO₂―CF₂―CF₂―O―CF₂―CF₂―(CF₂)q̄―CF₂―CF₂―C=C
                                       |
A    B    C    D   E    G    H   I  L  F N
``` wherein the chemical shifts δ (ppm from CFCl₃) turn out as follows: A=46.5; B=−114; C and D=83 to −84.8; E=−127; G=−122.7 to −123.6; N=−106.5; M=−90.5; L=190; I=−119 to −120; H=−125.

EXAMPLE 10

Into an autoclave of stainless steel with a holding capacity of 500 ml, fitted with two valves, gauge, breaking disc and rocking stirrer, there were introduced 10 g of a mixture of olefines with an average molecular weight of 520, prepared as described in example 9, dissolved in 200 ml of 1,1,2-trichloro-trifluoroethane.

The autoclave was then heated up to 70° C. By means of a compressor there was then introduced into it tetrafluoroethylene until reaching a pressure of 13 atm. Thereupon, by means of a liquid dosing pump there were introduced into the autoclave 25 mg of bis(4 tert-.butyl-cyclohexyl)peroxydicarbonate dissolved in 20 ml of 1,1,2-trichloro-trifluoroethane. The mass was then subjected for 90 minutes to stirring, whereafter it was cooled down to room temperature and from it was extracted a gelatinous product which was centrifuged and repeatedly washed with the same reaction solvent. There were thus obtained 17.5 g of a copolymer of a powdery aspect, which at the percentual analysis showed the presence of 0.70% of S which corresponded to a content of 25% molar of units derived from the sulphonated olefine.

The copolymer press-molded at 280° C. between the plates of a Carver press resulted in a transparent sheet which showed the characteristical infrared absorption at 6.8 micron due to the fluorosulphonyl group.

The differential thermal analysis carried out on a Perkin Elmer DSC-1 apparatus, with a heating rate of 8° C. per minute and in a nitrogen atmosphere, showed a transition of the first order of little importance at 310° C.

EXAMPLE 11

Into a deaerated 100 ml autoclave of stainless steel, fitted with a valve, a gauge, a rupture disc, heatable in an oil bath with sledge-stirrer, there were introduced 40 ml of 1,1,2-trichlorotrifluorocthane containing in solution 7 mg of di(ter-butyl)peroxide and 1.9 g of alpha-fluorosulphonyl-gamma-oxa-perfluoro-(omega-1)-alkenes prepared as described in example 9. and of an average molecular weight of 520.

After connection of the autoclave with the vacuum line and after cooling in liquid nitrogen, the autoclave was brought up to a pressure of 0.1 mmHg. Thereupon there were introduced by transfer in the gaseous state 4.5 grams of tetrafluoroethylene. The autoclave was then heated at 150° C. and left at that temperature for 2 hours. After cooling and after a new addition of 7 mg of the same peroxide in 5 ml of 1,1,2-trichlorotrifluoroethane and 4.0 g of tetrafluoroethylene, following the same method, the treatment was repeated for 2 hours at 150° C. At the end of the test, from the autoclave was extracted a gelatinous product which, repeatedly washed with 1,1,2-trichloro-trifluoroethane and then dried, had the aspect of white flakes and weighed 3.6 g.

In the reaction solvent, through gass-chromatography there were evidenced the same alkenes used as comonomers and with the same average molecular weight. The copolymer, pressure molded at 300° C. between the molding plates of a Carver press under a load of 8,000 kg., gave a transparent plate which under the infrared examination showed a maximum at 6.8 micron, typical for the SO₂F group, while there is missing the 5.6 micron band of the double perfluorovinyl bond.

The percentual analysis showed the presence of 0.41% by weight of sulphur corresponding to a content in units derived from sulphonated olefine of 1.4% molar.

EXAMPLE 12

Into a 500 ml autoclave of stainless steel, fitted with two valves, a gauge, a rupture disc and a rocking stirrer, there were introduced 32.3 g of the olefines of average molecular weight 520, prepared as described in example 9, dissolved in 200 ml of 1,1,2-trichlorotrifluoroethane.

By means of a compressor there was added a mixture consisting of 70 parts of hexafluoropropene and 30 parts of vinylidene fluoride until reaching a pressure of 7 atm; after heating to 80° C. there were added through a liquid dosing pump 0.7 g of bis (4-tert-butyl-cyclohexyl)peroxydicarbonate dissolved in 15 ml of 1,1,2-trichlorotrifluoroethane.

The reaction mass was then subjected to stirring for 3 hours after which it was allowed to cool down to room temperature; the residual gases were exhausted and from the autoclave was extracted a suspension of copolymer in the reaction solvent.

The copolymer was separated from the solvent, then washed repeatedly with 1,1,2-trichlorotrifluoroethane and dried, after which it was dissolved in acetone and reprecipitated with 1,1,2-trichlorotrifluoroethane. The copolymer was again dried.

A plate of the copolymer, under the infrared absorption analysis, besides the typical bands of the hexafluoroproene-vinylidene fluoride copolymers, showed also the characteristical bands of the —SO₂F group.

From the NMR analysis of the $^{19}F$ it appeared that difluoroethylene and trifluoromethyl units were present in a ratio of 8.5:1.5 besides that there were present units of ω-fluorosulphonyl-oxaperfluoroalkan-perfluoroethylene.

The percentual analysis showed the presence of 0.74% of S which corresponded to a content of 2% molar of units derived from the olefine according to this invention.

EXAMPLE 13

100 parts of the copolymer obtained as described in example 12 were admixed to 20 parts of carbon black MT, 5 parts of ZnO and 2 parts of ethylenediamine carbammate in a laboratory calendar with cylinders heated at 50° C.

The mixture was introduced into a Carver press with heatable cylinders, between polytetrafluoroethylene sheets and was heated for 3 hours at 150° C. under a load of 10,000 kg.

The sample was then post-treated in an oven with air circulation, for 8 hours at 150° C. On test specimens was then determined a breaking load of 100 kg/sq. cm and an elastic modulus $M_{100}=47$. One vulcanized plate was immersed in heptane for 48 hours at 70° C. and on it there was then measured a weight increase of 0.1% while the volume increased 1.3%.

From a plate of vulcanized product described above, having a thickness of 0.2 mm, there was obtained a disc which was mounted on a membrane pump, in such a way as to form the diaphragm between the operational control fluid and the fluid to be pumped. The pump with the membrane of the described material was used for pumping heptane at 75° C. and at 2 atm in a propylene polymerization installation. After 1,000 hours of operation no variations in the flow rate of the pump could be observed, which proves the excellent chemical and thermal resistance of the material against the swelling action of the hot heptane.

We claim:

1. A substituted fluoride of an oxafluoroalkansulphonic acid having the formula:

$$FSO_2-CFXCF_2-O-CF_2CFX-(CF_2CFX)_n-A$$

wherein A is I or F, X is independently selected from the group consisting of F, $CF_3$ and Cl and n is 0-4.

2. A compound according to claim 1, wherein A is I.
3. A compound according to claim 1, wherein A is F.
4. A compound according to claim 1, wherein n is from 1 to 4.
5. A compound according to claim 2, wherein n is from 1 to 4.
6. A compound according to claim 3, wherein n is from 1 to 4.
7. A compound according to claim 4, wherein X is F.
8. A compound according to claim 5, wherein X is F.
9. A compound according to claim 6, wherein X is F.
10. A compound having the formula:

$$FSO_2-CF_2CF_2-O-CF_2CF_2-(CF_2CF)_nA$$
$$\qquad\qquad\qquad\qquad\qquad\qquad |$$
$$\qquad\qquad\qquad\qquad\qquad\quad CF_3$$

wherein n is from 1 to 4, and wherein A is halogen selected from the group consisting of I and F.

11. A compound having the formula:

$$FSO_2-CF_2CF_2-O-CF_2CF_2-CF_2CF-(CF_2CF_2)_m-A$$
$$\qquad\qquad\qquad\qquad\qquad\qquad\qquad\quad |$$
$$\qquad\qquad\qquad\qquad\qquad\qquad\qquad CF_3$$

wherein m is from 1 to 3 and wherein A is a halogen selected from the group consisting of I and F.

* * * * *